United States Patent
Huculak et al.

(10) Patent No.: US 6,290,690 B1
(45) Date of Patent: Sep. 18, 2001

(54) SIMULTANEOUS INJECTION AND ASPIRATION OF VISCOUS FLUIDS IN A SURGICAL SYSTEM

(75) Inventors: John C. Huculak, Mission Viejo; Richard L. Zaleski, II, San Juan Capistrano; Russell L. Finlay, Dana Point, all of CA (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/336,922

(22) Filed: Jun. 21, 1999

(51) Int. Cl.$^7$ ................................................ A61M 31/00

(52) U.S. Cl. .................... 604/521; 604/35; 604/140; 604/141

(58) Field of Search ................................ 604/19, 27, 35, 604/43, 500, 521, 131, 140, 141; 433/101

(56) References Cited

U.S. PATENT DOCUMENTS

| | | | |
|---|---|---|---|
| 3,882,872 | * | 5/1975 | Douvas et al. . |
| 3,884,237 | * | 5/1975 | O'Malley et al. ............ 128/303.14 |
| 3,884,238 | * | 5/1975 | O'Malley et al. ................ 128/305 |
| 4,007,742 | * | 2/1977 | Banko ................................ 128/230 |
| 4,184,510 | | 1/1980 | Murry et al. ....................... 137/565 |
| 4,246,932 | | 1/1981 | Raines ................................ 137/512 |
| 4,274,411 | | 6/1981 | Dotson, Jr. ......................... 128/276 |
| 4,331,130 | * | 5/1982 | Lewicky . |
| 4,395,258 | | 7/1983 | Wang et al. .......................... 604/65 |
| 4,484,915 | | 11/1984 | Tartaglia ............................ 604/227 |
| 4,493,695 | | 1/1985 | Cook .................................... 604/27 |
| 4,627,833 | | 12/1986 | Cook .................................... 604/34 |
| 4,683,916 | | 8/1987 | Raines ................................ 137/854 |
| 4,713,051 | | 12/1987 | Steppe et al. ........................ 604/30 |
| 4,758,238 | | 7/1988 | Sundblom et al. ................ 604/319 |
| 4,790,816 | | 12/1988 | Sundblom et al. ................. 604/31 |
| 4,795,423 | * | 1/1989 | Osterholm .......................... 604/24 |
| 4,798,580 | | 1/1989 | DeMeo et al. ....................... 604/30 |
| 4,846,172 | * | 7/1989 | Berlin . |
| 5,066,276 | * | 11/1991 | Wang .................................. 604/51 |
| 5,120,307 | * | 6/1992 | Wang .................................. 604/51 |
| 5,267,956 | | 12/1993 | Beuchat .............................. 604/30 |
| 5,268,624 | * | 12/1993 | Zanger .............................. 318/551 |
| 5,328,481 | | 7/1994 | Wang .................................. 604/51 |
| 5,336,175 | | 8/1994 | Mames ................................ 604/49 |
| 5,336,487 | * | 8/1994 | Refojo et al. .................. 424/78.04 |
| 5,360,413 | | 11/1994 | Leason et al. ..................... 604/249 |
| 5,364,342 | | 11/1994 | Beuchat et al. .................... 604/30 |
| 5,370,630 | * | 12/1994 | Smidebush et al. .............. 604/209 |
| 5,429,601 | * | 7/1995 | Conley et al. ...................... 604/65 |
| 5,487,725 | * | 1/1996 | Peyman ............................... 604/22 |
| 5,582,595 | | 12/1996 | Haber et al. ....................... 604/187 |

(List continued on next page.)

FOREIGN PATENT DOCUMENTS

| | | | |
|---|---|---|---|
| 0 348 146 | 12/1989 | (EP) | ............................ A61F/9/00 |
| 0664898 | 2/1999 | (EP) | ............................ G05B/19/10 |
| 9808450 | 3/1998 | (WO) | ........................... A61B/17/20 |
| 9808451 | 3/1998 | (WO) | ........................... A61B/17/20 |
| 9808452 | 3/1998 | (WO) | ........................... A61B/17/20 |
| 9808453 | 3/1998 | (WO) | ........................... A61B/17/20 |
| 9914648 | 3/1999 | (WO) | .............................. G05G/1/14 |

*Primary Examiner*—Richard K. Seidel
*Assistant Examiner*—Cris Rodriguez
(74) *Attorney, Agent, or Firm*—W. David Lee (57) ABSTRACT

A method of injecting a first viscous fluid into a target tissue simultaneous with aspirating a second viscous fluid from the target tissue is disclosed. A surgical system is provided that is capable of supplying pneumatic pressure and vacuum. A first viscous fluid is injected into the target tissue using pneumatic pressure from the system. A mode of operation of the system is changed to provide vacuum and pneumatic pressure. The second viscous fluid is aspirated from the target tissue using vacuum from the system, and the pneumatic pressure remains substantially constant during aspiration. An improved foot pedal for controlling the simultaneous injection and aspiration of viscous fluids is also disclosed.

21 Claims, 3 Drawing Sheets

U.S. PATENT DOCUMENTS

| | | | |
|---|---|---|---|
| 5,639,796 | 6/1997 | Lee | 514/773 |
| 5,674,194 | 10/1997 | Jung et al. | 604/65 |
| 5,743,886 | 4/1998 | Lynn et al. | 604/191 |
| 5,814,010 | 9/1998 | Ziegler | 604/22 |
| 5,860,949 | 1/1999 | Chen | 604/35 |
| 5,868,728 * | 2/1999 | Giungo et al. | 606/1 |
| 5,928,663 * | 7/1999 | Peyman | 424/427 |
| 5,979,494 | 11/1999 | Perkins et al. | 137/487.5 |
| 5,984,889 * | 11/1999 | Christ et al. | 604/22 |
| 5,997,498 * | 12/1999 | De Juan, Jr. | 604/26 |

* cited by examiner

SIMULTANEOUS INJECTION AND ASPIRATION OF VISCOUS FLUIDS IN A SURGICAL SYSTEM

FIELD OF THE INVENTION

The present invention generally pertains to apparatus and methods for providing simultaneous viscous fluid injection and aspiration in a surgical system. More particularly, but not by way of limitation, the present invention pertains to apparatus and methods for injecting a long-term viscous fluid tamponade into the posterior segment of the eye while simultaneously aspirating a short-term viscous fluid tamponade out of the eye during vitreoretinal surgery.

DESCRIPTION OF THE RELATED ART

In a healthy human eye, the retina is physically attached to the choroid in a generally circumferential manner behind the pars plana. The vitreous humor, a transparent jelly-like material that fills the posterior segment of the eye, helps to cause the remainder of the retina to lie against, but not physically attach, to the choroid. A helpful analogy is to imagine the choroid as the walls of a swimming pool. The retina is like a wallpaper that is pressed against the walls of the swimming pool by the water in the pool, but is only physically attached to the walls at the top of the pool.

Sometimes a portion of the retina becomes detached from the choroid. Other times a portion of the retina may tear, allowing aqueous humor, and sometimes vitreous, to flow between the retina and the choroid. Both of these conditions result in a loss of vision.

To surgically repair these conditions, a surgeon typically inserts a vitrectomy probe into the posterior segment of the eye via an incision through the sclera in the pars plana. Such an incision is called a scleratomy. The surgeon typically also inserts a fiber optic light source and an infusion cannula into the eye via similar incisions, and may sometimes substitute an aspiration probe for the vitrectomy probe. While viewing the posterior segment under a microscope and with the aid of the fiber optic light source, the surgeon cuts and aspirates away vitreous using the vitrectomy probe to gain access to the retinal detachment or tear. The surgeon may also use the vitrectomy probe, scissors, a pick, and/or forceps to remove any membrane that has contributed to the retinal detachment or tear. During this portion of the surgery, a saline solution is typically infused into the eye via the infusion cannula to maintain the appropriate intraocular pressure.

Next, many surgeons inject a perfluorocarbon liquid into the posterior segment of the eye to cause the detached or torn portion of the retina to flatten against the choroid in the proper location. Once the detached or torn portion of the retina is properly located, the surgeon uses a diathermy probe or a laser to fuse portions of the detached retina in place.

Unfortunately, perfluorocarbon liquids are toxic when left in the eye for a period of weeks. Since a retinal tear or detachment takes a period of weeks to re-attach after the above-described surgical procedure, the short-term perfluorocarbon liquid tamponade must be removed from the eye at the latter portion of the surgical procedure and replaced with a long-term tamponade. This long-term tamponade can be an air/gas mixture or a viscous fluid, such as silicone oil. If silicone oil is used, it too must be extracted from the eye after the retina re-attaches because it is toxic when left in the eye for a period of months.

Conventionally, surgeons employ several techniques to perform this replacement of perfluorocarbon liquid with silicone oil, which is sometimes called a "fluid/fluid exchange". First, the surgeon may use a conventional vitreoretinal surgical system to inject silicone oil via a system generated injection pressure and an infusion cannula. An exemplary system is the Accurus® surgical system sold by Alcon Laboratories, Inc. of Fort Worth, Tex. As the silicone oil is injected, pressure increases in the eye. The increased pressure in the eye causes the perfluorocarbon liquid to passively flow into an extrusion cannula connected to the aspiration probe. The aspiration probe removes the perfluorocarbon liquid from the eye. Unfortunately, this technique requires the use of larger diameter (e.g. straight 20 gage) extrusion cannulas to allow sufficient passive flow without excessively elevated intraocular pressure. In contrast, surgeons prefer to use tapered and/or soft tip extrusion cannulas due to the additional level of safety provided should they accidentally come in contact with the retina.

Second, a surgeon may use such a conventional vitreoretinal surgical system to inject silicone oil via a system generated infusion pressure and an infusion cannula. As the intraocular pressure increases, the surgeon switches the mode of operation of the surgical system so that it provides vacuum for the aspiration probe instead of injection pressure for the infusion cannula. The surgeon then utilizes the aspiration probe with extrusion cannula to aspirate perfluorocarbon liquid from the eye to counteract the above-described rise in intraocular pressure. Next, the surgeon reconfigures the surgical system for injection pressure and injects more silicone oil into the posterior segment of the eye. This cycling between injecting silicone oil and aspirating perfluorocarbon liquid is continued until all the perfluorocarbon liquid is replaced with silicone oil. In this technique, the surgeon visually monitors the eye in an attempt to prevent the intraocular pressure from rising to a dangerously high level (a "hard eye" condition) or a dangerously low level (a "soft eye" condition). In addition, it is important to note that this cycling is required because conventional vitreoretinal surgical systems are not capable of supplying simultaneous injection and aspiration of viscous fluids. However, even when this technique is performed successfully, the intraocular pressure can vary above and below a desired intraocular pressure. This variance of the intraocular pressure may cause difficulty for the surgeon during the procedure, can be detrimental to the patient, and is especially prevalent with the preferred use of tapered and soft tip extrusion cannulas.

Third, the surgeon may employ the technique of using a conventional vitreoretinal surgical system and an aspiration probe to aspirate perfluorocarbon liquid, and a second, separate system to inject silicone oil. The use of two systems allows the simultaneous injection and aspiration of viscous fluids into the eye. However, the use of two systems requires the surgeon to operate and control both systems simultaneously, which can be difficult. The surgeon may be forced to utilize additional staff to help with the operation of at least one of the systems.

As mentioned hereinabove, different methods of tamponading the retina after vitreoretinal surgery exist that do not require the use of perfluorocarbon liquids. For example, the surgeon may utilize an air/gas mixture as a long-term tamponade. In this technique, the surgeon infuses air while all of the saline, resulting from the vitrectomy process, is aspirated. The air acts to re-position the retina against the choroid. A mixture of air and gas (typically a perfluorocarbon gas) is then injected into the air-filled eye replacing the infused air. The air/gas mixture is of a specific proportion resulting in an expanding air/gas bubble having an expansion rate that closely matches the rate at which air leaks from the eye. The air/gas bubble helps prevent regenerated aqueous humor from wetting the retina before it has had sufficient time to re-attach. The bubble typically lasts several days. Unfortunately, the use of an air/gas mixture as a long-term tamponade requires a very compliant patient. For example, patients must hold their head in certain positions for several hours a day to insure that the air/gas bubble prevents aqueous humor from wetting the retina. This type of long-term tamponade is therefore not suitable for elderly, young, and mentally disabled patients, or patients requiring air travel. In addition, during large retinal tear or detachment procedures, such "fluid/air" and "air/gas" exchanges can result in slippage of the retina, procedural complications, and more surgeon time.

Therefore, a need exists in vitreoretinal surgery for a surgical system and a method that provides long-term tamponading of the retina without the above-described limitations. The system and method should be easy for the surgeon to use, should maximize patient safety, and should be economically feasible.

SUMMARY OF THE INVENTION

One aspect of the present invention comprises a method of injecting a first viscous fluid into a posterior segment of an eye simultaneously with aspirating a second viscous fluid from the posterior segment. A surgical system is provided that is capable of supplying pneumatic pressure and vacuum. A first viscous fluid is injected into the posterior segment using pneumatic pressure from the system. A mode of operation of the system is changed to provide vacuum and pneumatic pressure. The second viscous fluid is aspirated from the posterior segment using vacuum from the system, and the pneumatic pressure exhibits a decrease of about twelve percent or less during the aspirating step.

In another aspect, the present invention comprises a surgical system for injecting a first viscous fluid into a target tissue simultaneous with aspirating a second viscous fluid from the target tissue. The surgical system includes an assembly capable of supplying pneumatic pressure and vacuum to at least one microsurgical instrument, and a foot pedal operatively coupled to the assembly. The foot pedal includes a first range of motion in a generally vertical plane in which the assembly supplies proportional pneumatic pressure, and a second range of motion in a generally vertical plane in which the assembly supplies a substantially constant pneumatic pressure and proportional vacuum.

In another aspect, the present invention comprises a surgical system for injecting a first retinal tamponading fluid into a posterior segment of an eye simultaneous with aspirating a second retinal tamponading fluid from the posterior segment. The system includes a single pneumatic assembly capable of supplying pneumatic pressure and vacuum. The system also includes a syringe having a hollow bore with a first end and a second end, and a plunger movably disposed in the hollow bore between the first and second ends. The system further includes tubing fluidly coupling the first end of the hollow bore to the assembly. A volume of the tubing and the hollow bore on a side of the plunger nearest to the first end is greater than the volume of the posterior segment. This volume of the tubing and the hollow bore allows the assembly to supply a substantially constant pneumatic pressure to the side of the plunger nearest to the first end of the hollow bore simultaneous with supplying vacuum to aspirate the second retinal tamponading fluid.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 5 of the drawings, like numerals being used for like and corresponding parts of the various drawings.

Figure 1:
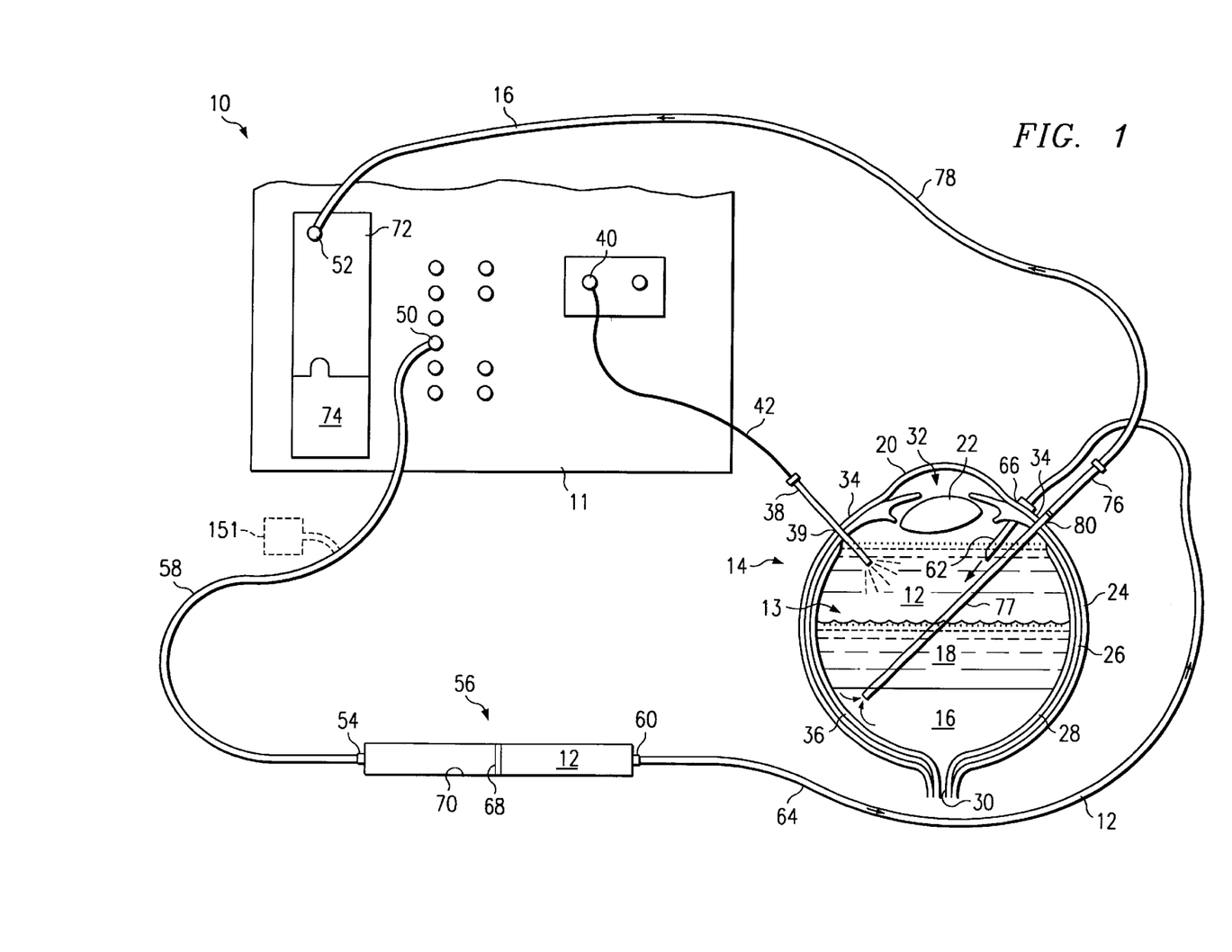
FIG. 1 is a schematic, fragmentary, partially sectional illustration of a surgical system for injecting a viscous fluid into a human eye while simultaneously aspirating a second viscous fluid from the eye according to a preferred embodiment of the present invention.

FIG. 1 shows a schematic illustration of a surgical system 10 injecting a viscous fluid 12 into a posterior segment 13 of a human eye 14 while simultaneously aspirating a second viscous fluid 16 out of eye 14 according to a preferred method of the present invention. Surgical system 10 is preferably a conventional surgical system capable of performing vitreoretinal surgery that has been modified according to the present invention. An exemplary surgical system 10 suitable for such modification is the Accurus® surgical system sold by Alcon Laboratories, Inc. When surgical system 10 is used to perform a "fluid/fluid exchange" as a portion of a surgery to repair a detached or torn retina, viscous fluid 12 is preferably silicone oil, and viscous fluid 16 is preferably perfluorocarbon liquid. In addition, a saline solution 18 is typically present within posterior segment 13. Silicone oil 12 preferably has a viscosity of about 1000 to about 5000 centistokes. Perfluorocarbon liquid 16 preferably has a viscosity of about 6 to about 7 centistokes. Saline solution 18 preferably has a viscosity of about 1 centistoke. An exemplary silicone oil suitable for use as silicone oil 12 is the Silikon™ silicone oil available from Alcon Laboratories, Inc. An exemplary perfluorocarbon liquid suitable for perfluorocarbon liquid 16 is Perfluoron® perfluorocarbon liquid sold by Alcon Laboratories, Inc. An exemplary saline solution suitable for saline solution 18 is BSS PLUS® intraocular irrigating solution sold by Alcon Laboratories, Inc.

Eye 14 has a cornea 20, a lens 22, a sclera 24, a choroid 26, a retina 28, and an optic nerve 30. Cornea 20 and lens 22 generally define an anterior segment 32 of eye 14. Lens 22, choroid 26, and retina 28 generally define posterior segment 13 of eye 14. Retina 28 is physically attached to choroid 26 in a circumferential manner proximate pars plana 34.

As shown in FIG. 1, eye 14 has undergone a vitrectomy process in which the vitreous humor has been cut and aspirated out of posterior segment 13, as described hereinabove. During this process, saline solution 18 was infused into eye 14 via an infusion cannula 62 to maintain the appropriate intraocular pressure. Also during this process, a detached portion or tear 36 of retina 28 was repositioned by injecting perfluorocarbon liquid 16 into posterior segment 13 via an injection cannula and syringe (not shown) to cause detached portion or tear 36 to flatten against choroid 26 in the proper location. Once portion or tear 36 was properly located, a diathermy probe or a laser (not shown) was used to fuse portion or tear 36 in place. During this process, a conventional fiber optic light source 38 provided light for the surgeon, who viewed posterior segment 13 via a microscope. Light source 38 is inserted into posterior segment 13 via a scleratomy 39. Light source 38 is preferably operatively coupled to a port 40 of surgical system 10 via light fiber cabling 42.

As described hereinabove, perfluorocarbon liquid 16 is toxic when left in eye 14 for a period of weeks. Since detached portion or tear 36 of retina 28 requires a period of weeks to re-attach after the above-described surgical procedure, perfluorocarbon liquid 16 is only acceptable as a short-term tamponade to hold portion or tear 36 of retina 28 in the proper location against choroid 26. Therefore, perfluorocarbon liquid 16 is removed from eye 14 and replaced with silicone oil 12, a long-term tamponade.

Surgical system 10 includes a port 50 capable of providing proportional pressure to a microsurgical instrument connected thereto. For the preferred fluid/fluid exchange of the present invention, port 50 is fluidly coupled to an end 54 of a conventional syringe 56 via tubing 58. A second end 60 of syringe 56 is fluidly coupled to infusion cannula 62 via tubing 64. Tubing 58 and 64 are preferably conventional PVC tubing. Infusion cannula 62 is inserted into posterior segment 13 via a scleratomy 66. Syringe 56 has a plunger 68 movably disposed within its hollow body 70.

Surgical system 10 also includes a port 52 capable of providing proportional vacuum to a microsurgical instrument attached thereto. Port 52 is preferably a part of conventional surgical cassette 72 that helps manage the aspiration flows of surgical system 10. U.S. Pat. Nos. 4,493,695; 4,627,833 (Cook); 4,395,258 (Wang et al.); 4,713,051 (Steppe et al.); 4,798,850 (DeMeo et al.); 4,758, 238; 4,790,816 (Sundblom et al.); 5,267,956; and 5,364,342 (Beuchat) all disclose tubeless or tube-type surgical cassettes and are incorporated herein in their entirety by reference. A collection bag 74 is fluidly coupled to surgical cassette 72.

For the preferred fluid/fluid exchange of the present invention, port 52 is fluidly coupled to an aspiration probe 76 having an extrusion cannula 77 via tubing 78. Tubing 78 is preferably conventional PVC tubing. Aspiration probe 76 and extrusion cannula 77 are inserted into posterior segment 13 via a scleratomy 80.

Figure 2:
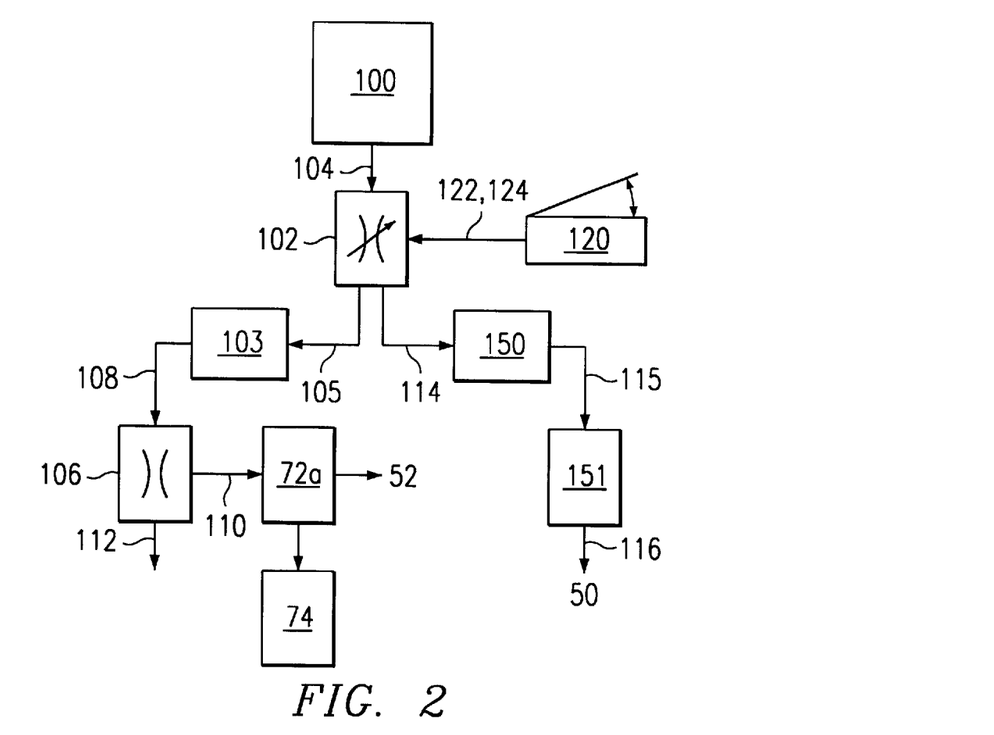
FIG. 2 is a block diagram of certain portions of the electronic and pneumatic subassemblies of the surgical system of FIG. 1.

FIG. 2 shows a block diagram of certain portions of the electronic and pneumatic sub-assemblies of surgical system 10. Surgical system 10 includes a regulated pneumatic pressure source 100 that is fluidly coupled to a proportional valve 102 via an input manifold 104. Pressure source 100 preferably supplies a constant source of pneumatic pressure on the order of about 85 psi. A suitable proportional valve for valve 102 is Model No. 002-AXXAVCAA sold by Porter Instrument Company, Inc. of Hatfield, Pa. Of course, other proportional valves may be used for valve 102. Proportional valve 102 is fluidly coupled to a solenoid valve 103 via a first valve output manifold 105. A vacuum pump or venturi 106 is fluidly coupled to solenoid valve 103 via a manifold 108. A suitable vacuum pump (venturi) for pump 106 is Model No. LX10 sold by PIAB of Hingham, Mass. Of course, other pumps or venturis may be used for pump 106. Pump 106 has a vacuum manifold 110 that is fluidly coupled to a volume 72a of surgical cassette 72 and to port 52. Pump 106 also has an exhaust manifold 112. In addition, proportional valve 102 is fluidly coupled to a solenoid valve 150 via a second valve output manifold 114. A reservoir 151 is fluidly coupled to solenoid valve 150 via a manifold 115. A manifold 116 fluidly couples reservoir 151 to port 50. The above-described portions of surgical system 10 in FIG. 2, with the exception of solenoid valves 103 and 150, reservoir 151, and manifolds 115 and 116, are conventional.

As is explained in more detail hereinbelow, a surgeon can switch the output of proportional valve 102 by opening and closing solenoid valves 103 and 150. When solenoid valve 103 is open and solenoid valve 150 is closed, proportional valve 102 supplies vacuum to port 52. When solenoid valve 150 is open and solenoid valve 103 is closed, proportional valve 102 supplies pneumatic pressure to port 50.

In surgical system 10, the surgeon chooses the desired vacuum or pressure level by manipulating a variable input device 120. Variable input device 120 is preferably a foot switch or foot pedal. Foot pedal 120 is operatively coupled to proportional valve 102 via conventional electronic cabling 122. A surgeon chooses the desired level of vacuum for port 52 or pressure for port 50 by manipulating foot pedal 120 to generate an input signal 124 for proportional valve 102. More specifically, the surgeon can gradually open proportional valve 102 by depressing foot pedal 120 and can gradually close proportional valve 102 by "letting up" on foot pedal 120. The degree to which proportional valve 102 is open determines the pressure and air flow rate delivered to manifold 105 or manifold 114. The greater the air flow through proportional valve 102, the greater the vacuum supplied to port 52, or the greater the pressure supplied to port 50. Although not shown in the block diagram of FIG. 2, a process control system is preferably operatively coupled to proportional valve 102, vacuum pump 106, vacuum manifold 110, second valve output manifold 114, and foot pedal 102 so as to give the surgeon precise control of the microsurgical instruments coupled to ports 50 or 52 of surgical system 10. The preferred process control system is described in detail in U.S. Pat. No. 5,674,194, which is commonly owned with the present invention and is incorporated herein in its entirety by reference.

Figure 3:
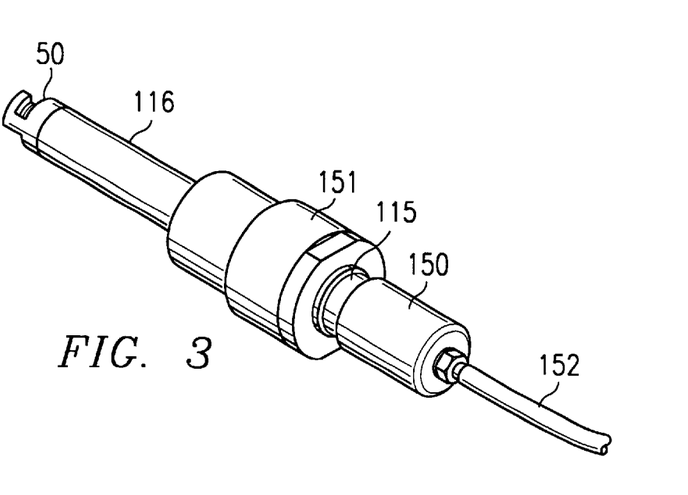
FIG. 3 shows a preferred embodiment of a pneumatic reservoir of the surgical system of FIG. 1.

FIG. 3 illustrates preferred embodiments of solenoid valve 150 and reservoir 151. Tubing 152 supplies pneumatic pressure from second valve output manifold 114 to solenoid valve 150, manifold 115, reservoir 151, manifold 116, and port or pneumatic connector 50. Tubing 152 is preferably conventional PVC tubing. Tubing 152, solenoid valve 150, manifold 115, reservoir 151, and manifold 116 are preferably located within housing 11 of surgical system 10 generally behind port 50.

Although not shown in FIG. 3, reservoir 151 may also be located external to housing 11 of surgical system 10. For example, reservoir 151 may be fluidly coupled to tubing 58, as shown schematically in FIG. 1. As another example, syringe 56 may be modified from its conventional form to include reservoir 151 proximate its end 54. As a further example, the length and/or inner diameter of tubing 58 may be modified from its conventional form so as to incorporate the volume of reservoir 151.

Figure 4:
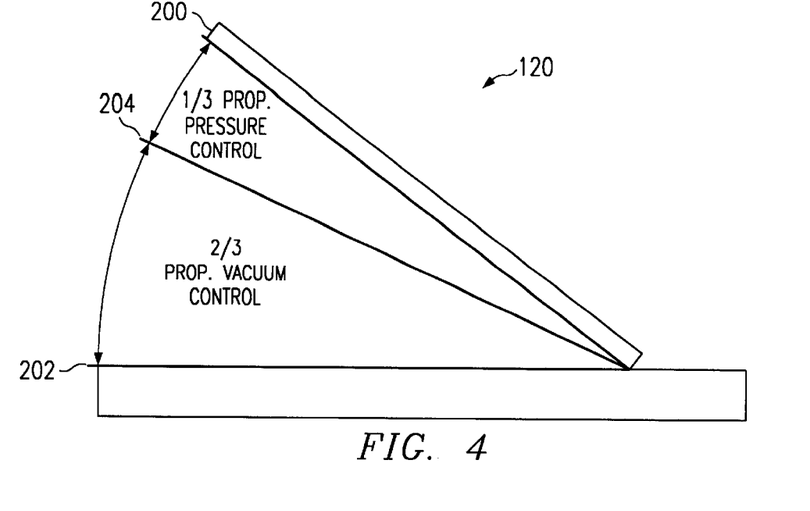
FIG. 4 is a schematic illustration of a preferred embodiment of a foot pedal of the surgical system of FIG. 1.

FIG. 4 schematically illustrates a preferred embodiment of foot pedal 120 according to the present invention. Foot pedal 120 has a first position 200 corresponding to a fully undepressed position, a second position 202 corresponding to a fully depressed position, and a third position 204 corresponding to an about one-third depressed position. Position 204 is preferably indicated by a mechanical detent of foot pedal 120. Foot pedal 120 may be made by modifying the conventional foot pedal sold as part of the Accurus® surgical system mentioned hereinabove.

A conventional surgical system 10 is limited by the fact that it cannot supply pneumatic pressure to port 50 for the injection of viscous fluid 12 into eye 14 simultaneously with supplying vacuum to port 52 for the aspiration of viscous fluid 16 from eye 14. However, the addition of solenoid valve 150, reservoir 151, and manifolds 115 and 116 enable the delivery of a substantially constant pneumatic pressure to port 50 while proportional vacuum is also provided to port 52. Significantly, this ability allows the surgeon to minimize the potential of slippage of retina 28 and to maintain the intraocular pressure of eye 14 at a level very close to the desired intraocular pressure during the fluid/fluid exchange.

Referring again to FIGS. 1 and 2, a first volume $V_1$ may be defined by the volume of air within manifold 115, reservoir 151, manifold 116, tubing 58, and syringe 56 on the side of plunger 68 proximate tubing 58. A second volume $V_2$ may be defined by the volume of posterior segment 13 of eye 14 to be filled with silicone oil 12. As silicone oil 12 is injected into eye 14, syringe plunger 68 moves toward end 60 of syringe 56, increasing the volume of $V_1$ by the amount of oil injected. When all of the posterior segment 13 of eye 14 is filled with silicone oil 12, volume $V_1$ will have increased by an amount $V_2$. By using reservoir 151 to make volume $V_1$ substantially larger than volume $V_2$, the silicone oil injection pressure can be maintained at a substantially constant pressure. More specifically, defining the initial silicone oil injection pressure in $V_1$ as $P_1$ and the post-injection pressure as $P_2$ with a volume of $V_1+V_2$, Boyle's Law shows that $P_1$ will be approximately equal to $P_2$ if $V_2$ is small with respect to $V_1$: $P_2=P_1 \times (V_1/(V_1+V_2)) \Rightarrow P_2 \cong P_1$, if $V_1 \cong V_1+V_2$ when $V_2 \ll V_1$.

At some point during the injection of silicone oil 12, the surgeon will also begin aspirating perfluorocarbon liquid 16 to counteract the rise in intraocular pressure caused by the injection of silicone oil 12. As is explained in more detail hereinbelow, when a surgeon initiates aspiration of perfluorocarbon liquid 16 from posterior segment 13, solenoid valve 150 closes, eliminating the pneumatic pressure supplied from proportional valve 102, but isolating the silicone oil injection pressure in manifold 115, reservoir 151, manifold 116, tubing 58, and syringe 56. The isolated silicone oil injection pressure insures continued flow of silicone oil 12 into eye 14 via tubing 64.

Figure 5:
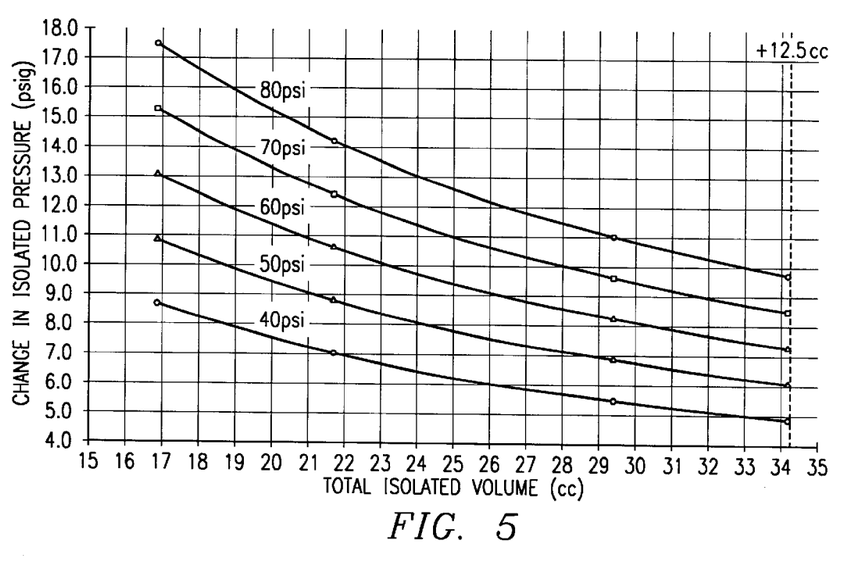
FIG. 5 is a graphic illustration of the change in injection pressure in the surgical system of FIG. 1.

FIG. 5 further illustrates how reservoir 151 functions to keep silicone oil injection pressure $P_1$ substantially constant during the injection of silicone oil 12. For one preferred embodiment of surgical system 10, tubing 58 and syringe 56 on the side of plunger 68 proximate tubing 58 have a volume $V_0$ of about twenty two (22) cubic centimeters, and reservoir 151 has a volume of about 12.5 cubic centimeters. For a typical adult human eye, the volume $V_2$ of posterior segment 13 to be filled with silicone oil 12 is about 5 cubic centimeters. When $V_0$ was increased by $V_2$, as would occur during the injection of 5 cubic centimeters of silicone oil, an injection pressure $P_0$ of about 40 psi decreased about 7 psig (about 17.5 percent). In contrast, with a reservoir 151 having a volume of 12.5 cubic centimeters added to $V_0$ for a total volume $V_1$ of about 34.5 cubic centimeters, an injection pressure $P_1$ of about 40 psi decreased only about 4.8 psig (about 12 percent) when $V_1$ was increased by $V_2$. As another example, an injection pressure $P_0$ of about 80 psi decreased about 14 psig (about 17.5 percent) when $V_0$ was increased by $V_2$. In contrast, with a reservoir 151 having a volume of 12.5 cubic centimeters added to $V_0$ for a total volume $V_1$ of about 34.5 cubic centimeters, an injection pressure $P_1$ of about 80 psi decreased only about 9.8 psig (about 12 percent) when $V_1$ was increased by $V_2$. Similar variances of $P_1$ were observed for injection pressures of 50 psi, 60 psi, and 70 psi, as shown in FIG. 5. Boyle's Law shows that the variance of $P_1$ may be reduced below 12 percent by increasing the volume of reservoir 151, if desired, for specific surgical systems 10. For example, this variance of $P_1$ may be reduced to 10 percent, 8 percent, 6 percent, 4 percent, 2 percent, or below.

Referring to FIGS. 1 through 5, the preferred method of operating foot pedal 120 according to the present invention so as to perform a fluid/fluid exchange of perfluorocarbon liquid 16 and silicone oil 12 is described in greater detail. When foot pedal 120 is in position 200, proportional valve 102 does not supply pneumatic pressure or vacuum to ports 50 or 52, respectively. Solenoid valve 103 is in the closed position, and solenoid valve 150 is in the open position. Silicone oil 12 is not being injected into posterior segment 13 via infusion cannula 62, and perfluorocarbon liquid 16 is not being aspirated via aspiration probe 76.

When a surgeon gradually moves foot pedal 120 from position 200 to position 204, pneumatic pressure is supplied to manifold 115, reservoir 151, manifold 116, port 50, tubing 58, and syringe 56 in gradually increasing amounts. This is accomplished via a change in electrical signal 124 from foot pedal 120 to proportional valve 102 communicated via electrical cabling 122. The minimum pneumatic pressure is preferably 0 psi (position 200), and the maximum pneumatic pressure is preferably about 80 psi (position 204). Such proportional pneumatic pressure causes silicone oil 12 from syringe 56 and tubing 64 to be injected into posterior segment 13 via infusion cannula 62. During this process, a clamping mechanism (not shown) within surgical cassette 72 is preferably in the closed position to prevent passive flow of perfluorocarbon liquid 16 into surgical cassette 72. Therefore, the intraocular pressure of eye 14 gradually begins to rise.

If the surgeon applies additional downward force to foot pedal 120 at position 204, he or she overcomes a mechanical detent in foot pedal 120. While overcoming this detent, the printed circuit board electronics of surgical system 10 close solenoid valve 150 and open solenoid valve 103, fluidly coupling vacuum pump 106 to first valve output manifold 105. Closure of solenoid valve 150 causes the injection pressure $P_1$ in manifold 115, reservoir 151, manifold 116, port 50, tubing 58, and syringe 56 to be maintained, resulting in the continued flow of silicone oil into eye 14 via tubing 64. Furthermore, the printed circuit board electronics of surgical system 10 actuate the clamping mechanism within surgical cassette 72 to an open position allowing flow of perfluorocarbon liquid 16 from tubing 78 into cassette 72.

When a surgeon gradually moves foot pedal 120 from position 204 to position 202, vacuum is supplied to port 52, tubing 78, aspiration probe 76, and extrusion cannula 77 in increasing amounts. This is accomplished via a change in electrical signal 124 from foot pedal 120 to proportional valve 102 communicated via electrical cabling 122. The minimum vacuum is preferably 0 mmHg (position 204), and the maximum vacuum is preferably about 600 mmHg (position 202). Such proportional vacuum causes perfluorocarbon liquid 16 to be aspirated from posterior segment 13 into cassette 72 and collection bag 74. This vacuum counteracts the rise in intraocular pressure caused by the injection of silicone oil 12.

As the intraocular pressure begins to decrease due to aspiration of perfluorocarbon liquid 16, the surgeon lets up on foot pedal 120, controlling the flow of aspirated perfluorocarbon liquid 16 to more closely match the injection flow rate of silicone oil 12. In this manner, the surgeon quickly brings the intraocular pressure to its desired level.

During this replacement of perfluorocarbon liquid 16 with silicone oil 12, the surgeon visually monitors eye 14 to prevent the intraocular pressure from rising to a dangerously high level (a "hard eye" condition) or to a dangerously low level (a "soft eye" condition). Significantly, because of the added volume of reservoir 151 and solenoid valve 150, the silicone oil injection pressure $P_1$ remains substantially constant during the aspiration of perfluorocarbon liquid 16. This, combined with the design of foot pedal 120, allows the surgeon to more effectively control the intraocular pressure of eye 14, minimizing risk to the patient.

From the above, it may be appreciated that the present invention provides improved apparatus and methods for tamponading a retinal tear or detachment. The present invention minimizes retinal slippage and variations in intraocular pressure during a fluid/fluid exchange. The present invention also provides the surgeon with an easier method of controlling a fluid/fluid exchange.

The present invention is illustrated herein by example, and various modifications may be made by a person of ordinary skill in the art. For example, although the preferred apparatus and methods are described hereinabove in connection with a fluid/fluid exchange of perfluorocarbon liquid and silicone oil in vitreoretinal surgery, the present invention is applicable to the simultaneous injection and aspiration of other viscous fluids. As another example, the present invention is also applicable to other types of surgeries other than vitreoretinal surgery.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of injecting a first viscous fluid into a posterior segment of an eye simultaneous with aspirating a second viscous fluid from said posterior segment, comprising the steps of:
   providing a surgical system capable of supplying pneumatic pressure and vacuum;
   injecting said first viscous fluid into said posterior segment using pneumatic pressure from said system;
   changing a mode of operation of said system to provide vacuum and pneumatic pressure; and
   aspirating said second viscous fluid from said posterior segment using vacuum from said system;
   wherein said pneumatic pressure exhibits a decrease of about twelve percent or less during said aspirating step.

2. The method of claim 1 wherein said eye is a a human eye.

3. The method of claim 1 wherein said first viscous fluid comprises a silicone oil, said second viscous fluid comprises a perfluorocarbon liquid.

4. A surgical system for injecting a first retinal tamponading fluid into a posterior segment of an eye simultaneous with aspirating a second retinal tamponading fluid from said posterior segment, said posterior segment having a volume, comprising:
   a single pneumatic assembly capable of supplying pneumatic pressure and vacuum, said assembly comprising:
      a regulated pressure source;
      a proportional valve fluidly coupled to said regulated pressure source;
      a vacuum pump fluidly coupled to said proportional valve; and
      a reservoir fluidly coupled to said proportional valve;
   a syringe having:
      a hollow bore with a first end and a second end; and
      a plunger movably disposed in said hollow bore between said first end and said second end; and
   tubing fluidly coupling said first end of said hollow bore on a side assembly;
   wherein a volume of said reservoir, said tubing, and said hollow bore on a side of said plunger proximate said first end is greater than said volume of said posterior segment.

5. The surgical system of claim 4 further compressing:
   an infusion cannula fluidly coupled to said syringe;
   an aspiration probe fluidly coupled to said assembly; and
   an extrusion cannula coupled to said aspiration probe.

6. The surgical system of claim 5 wherein said infusion cannula end said extrusion cannula are for insertion into said posterior segment.

7. The surgical system of claim 4 further comprising a housing and wherein:
   said assembly is disposed within said housing;
   said reservoir is fluidly coupled with said tubing and said syringe; and
   said tubing and said syringe are disposed outside of said housing.

8. A surgical system for injecting a first viscous fluid into a target tissue simultaneous with aspirating a second viscous fluid from said target tissue, comprising:
   an assembly capable of supplying pneumatic pressure and vacuum to at least one microsurgical instrument;
   a foot pedal, operatively coupled to said assembly, comprising:
      a first range of motion in a generally vertical plane in which said assembly supplies proportional pneumatic pressure; and
      a second range of motion in a generally vertical plane in which said assembly supplies a substantially constant pneumatic pressure and proportional vacuum.

9. The surgical system of claim 8 wherein said foot pedal comprises a mechanical detent separating said first range of motion and said second range of motion.

10. The surgical system of claim 9 wherein said first range of motion is from a first position corresponding to a fully undepressed position, to a second position corresponding to said mechanical detent.

11. The surgical system of claim 10 wherein said second range of motion is from said second position to a third position corresponding to a fully depressed position.

12. The surgical system of claim 11 wherein moving said foot pedal in said first range of motion toward said second position increases an amount of pneumatic pressure supplied by said assembly.

13. The surgical system of claim 11 wherein moving said foot pedal in said second range of motion toward said third position increases an amount of vacuum supplied by said assembly.

14. The surgical system of claim 8 wherein said first range of motion comprises about one third of a full range of motion in a generally vertical plane of said foot pedal.

15. The surgical system of claim 8 further comprising:

an infusion cannula and a syringe for injecting said first viscous fluid into said target tissue; and an aspiration probe and an extrusion cannula for aspirating said second viscous fluid from said target tissue.

16. The surgical system of claim 8 wherein said substantially constant pneumatic pressure comprises a pneumatic pressure decrease of about twelve precent or less.

17. A surgical system for injecting a silicone oil into a posterior segment of an eye simultaneous with aspirating a perfluorocarbon liquid from said posterior segment, said posterior segment having a volume, comprising:

a single pneumatic assembly capable of supplying pneumatic pressure and vacuum, said assembly comprising:
a regulated pressure source
a proportional valve fluidly coupled to said regulated pressure source;
a vacuum pump fluidly coupled to said proportional valve; and
a reservoir fluidly coupled to said proportional valve;

a syringe having:
a hollow bore with a first end and a second end; and
a plunger movably disposed in said hollow bore between said first end and said second end; and tubing fluidly coupling said first end of said hollow bore to said assembly;

wherein a volume of said reservoir, said tubing, and said hollow bore on a side of said plunger proximate said first end is greater than said volume of said posterior segment.

18. A surgical system for injecting a first retinal tamponading fluid into a posterior segment of an eye simultaneous with aspirating a second retinal tamponading fluid from said posterior segment, comprising:

an assembly capable of supplying pneumatic pressure and vacuum to at least one microsurgical instrument;

a foot pedal, operatively coupled to said assembly, comprising:
a first range of motion in a generally vertical plane in which said assembly supplies proportional pneumatic pressure; and
a second range of motion in a generally vertical plane in which said assembly supplies a substantially constant pneumatic pressure and proportional vacuum.

19. The surgical system of claim 18 wherein said substantially constant pneumatic pressure comprises a pneumatic pressure decrease of about twelve percent or less.

20. A surgical system for injecting a silicone oil into a posterior segment of an eye simultaneous with aspirating a perfluorocarbon liquid from said posterior segment, comprising:

an assembly capable of supplying pneumatic pressure and vacuum to at least one microsurgical instrument;

a foot pedal, operatively coupled to said assembly, comprising:
a first range of motion in a generally vertical plane in which said assembly supplies proportional pneumatic pressure; and
a second range of motion in a generally vertical plane in which said assembly supplies a substantially constant pneumatic pressure and proportional vacuum.

21. The surgical system of claim 20 wherein said substantially constant pneumatic pressure comprises a pneumatic pressure decrease of about twelve percent or less.

* * * * *

UNITED STATES PATENT AND TRADEMARK OFFICE
CERTIFICATE OF CORRECTION

PATENT NO. : 6,290,690 B1
DATED : September 18, 2001
INVENTOR(S) : Huculak, John C., Zaleski, II, Richard L. and Finlay, Russell L.

It is certified that error appears in the above-identified patent and that said Letters Patent is hereby corrected as shown below:

Column 3,
Lines 46-63, delete the entire paragraph beginning with "In another aspect" and ending with "retinal tamponading fluid."

Signed and Sealed this

Twenty-third Day of July, 2002

Attest:

JAMES E. ROGAN
Attesting Officer   Director of the United States Patent and Trademark Office